United States Patent [19]

Angerbauer et al.

[11] Patent Number: 5,177,080
[45] Date of Patent: Jan. 5, 1993

[54] SUBSTITUTED PYRIDYL-DIHYDROXY-HEPTENOIC ACID AND ITS SALTS

[75] Inventors: Rolf Angerbauer; Peter Fey; Walter Hübsch, all of Wuppertal; Thomas Philipps, Cologne; Hilmar Bischoff, Wuppertal; Dieter Petzinna, Duesseldorf; Delf Schmidt, Wuppertal, all of Fed. Rep. of Germany; Günter Thomas, Milan, Italy

[73] Assignee: Bayer Aktiengesellschaft, Leverkusen, Fed. Rep. of Germany

[21] Appl. No.: 798,675

[22] Filed: Nov. 26, 1991

[30] Foreign Application Priority Data

Dec. 14, 1990 [DE] Fed. Rep. of Germany ....... 4040026
Jul. 31, 1991 [IT] Italy .............................. 91 A/002125

[51] Int. Cl.⁵ ..................... A01K 31/44; C07D 213/26; C07D 213/55; C07D 213/56
[52] U.S. Cl. .................................. 514/277; 546/342; 546/335; 562/401
[58] Field of Search ................ 546/342, 335; 514/277; 562/401

[56] References Cited

U.S. PATENT DOCUMENTS 4,906,624  3/1990  Chucholowski ................... 546/193

Primary Examiner—C. Warren Ivy
Assistant Examiner—Phyllis Spivack
Attorney, Agent, or Firm—Sprung Horn Kramer & Woods

[57] ABSTRACT

Substituted pyridyl-dihydroxy-heptenoic acid of the formula

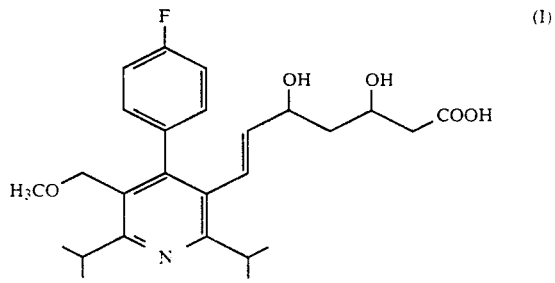

(I)

and its salts, if desired in an isomeric form, have a superior inhibitory action on HMG-CoA reductase and thus bring about a surprisingly good lowering of the cholesterol content in the blood.

9 Claims, No Drawings

SUBSTITUTED PYRIDYL-DIHYDROXY-HEPTENOIC ACID AND ITS SALTS

The invention relates to a substituted pyridyl-dihydroxyheptenoic acid, its salts, a process for its preparation, and its use in medicaments.

It has been disclosed that lactone derivatives isolated from fungal cultures are inhibitors of 3-hydroxy-3-methyl-glutaryl coenzyme A reductase (HMG-CoA reductase) [mevinolin, EP 22,478; US-4,231,938].

It is additionally known that pyridine-substituted dihydroxyheptenoic acids are inhibitors of HMG-CoA reductase [EP 325,130; EP 307,342; EP 306,929].

It has now been found that the substituted pyridyl-dihydroxy-heptenoic acid of the formula

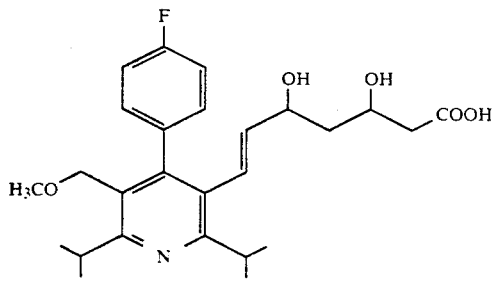
(I)

and its salts, if desired in an isomeric form, have a superior inhibitory action on HMG-CoA reductase and thus bring about a surprisingly good lowering of the cholesterol content in the blood.

The substituted pyridyl-dihydroxy-heptenoic acid according to the invention can be present in the form of its salts. In general, salts with organic or inorganic bases may be mentioned here.

In the context of the present invention, physiologically acceptable salts are preferred. Physiologically acceptable salts of the substituted pyridyl-dihydroxy-heptenoic acid according to the invention can be metal or ammonium salts. Preferred salts which may be mentioned are sodium, potassium, magnesium or calcium salts and also ammonium salts which are derived from ammonia or organic amines, such as, for example, methylamine, ethylamine, propylamine, isopropylamine, di- or triethylamine, diisopropylamine, di- or triethanolamine, dicyclohexylamine, arginine, lysine or ethylenediamine. Sodium and potassium salts are particularly preferred.

The substituted pyridyl-dihydroxy-heptenoic acid according to the invention and its salts have two asymmetric carbon atoms, namely the two carbon atoms to which the hydroxyl groups are bonded, and can therefore exist in various stereochemical forms. The invention relates both to the individual isomers and to their mixtures. Thus, the substances according to the invention can be present, depending on the relative position of the hydroxyl groups, in the erythro configuration or in the threo configuration:

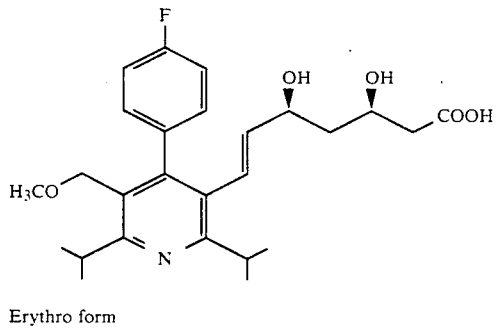
Erythro form

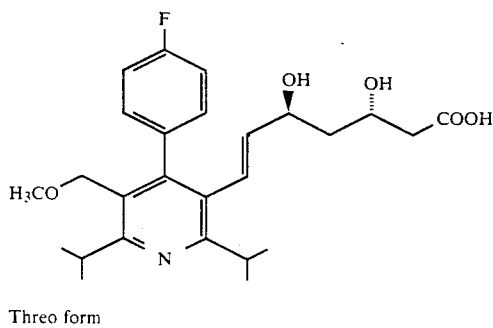
Threo form

The erythro configuration is preferred.

Two enantiomers each exist in turn both of the substances in the threo and in the erythro configuration, namely of the 3R,5R-isomer and the 3S,5R-isomer (erythro form) and of the 3R,5R-isomer and the 3S,5S-isomer (threo form). Of these, the 3R,5S/3S,5R racemates and the 3R,5S enantiomers are preferred.

The substances according to the invention can moreover be present in the E configuration or the Z configuration owing to the double bond. Those compounds which have the E configuration are preferred.

The (+)-enantiomers of the substituted pyridyl-dihydroxyheptenoic acid in the erythro (E) configuration and its salts are particularly preferred.

The substituted pyridyl-dihydroxy-heptenoic acid of the formula (I)

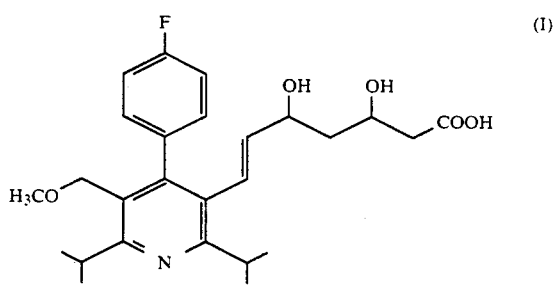
(I)

and its salts, if desired in an isomeric form, are prepared by

[A] in the case of the racemic products, hydrolysing the corresponding racemic esters of the formula (II)

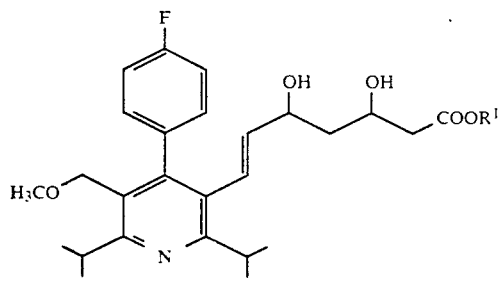
(II)

in which
R$^1$- represents C$_1$-C$_4$-alkyl or benzyl, or

[B] in the case of the stereoisomerically homogeneous products
first converting the racemic esters of the formula (II)
using the (+)- or (−)-enantiomeric amine of the formula (III)

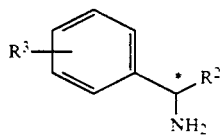
(III)

in which
R$^2$- represents C$_1$-C$_4$-alkyl which is optionally substituted by hydroxyl
and
R$^3$- represents hydrogen, halogen, C$_1$-C$_4$-alkyl or C$_1$-C$_4$-alkoxy, into the corresponding diastereomeric amides of the formula (IV)

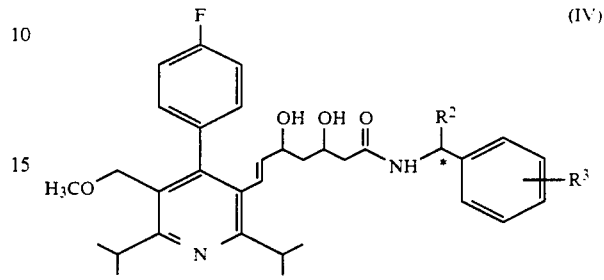
(IV)

separating the mixture of the diastereomeric amides into the individual diastereomers by chromatography or crystallisation,
and then hydrolysing the pure diastereomeric amides to give the enantiomerically pure products.

The process is intended to be illustrated by way of example in the following scheme:

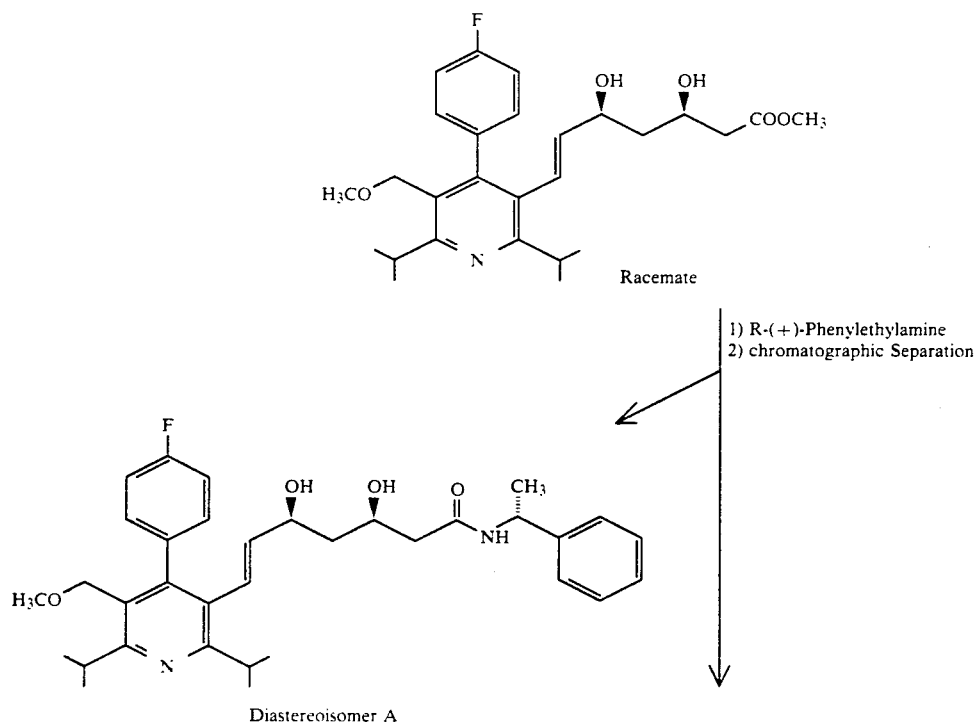

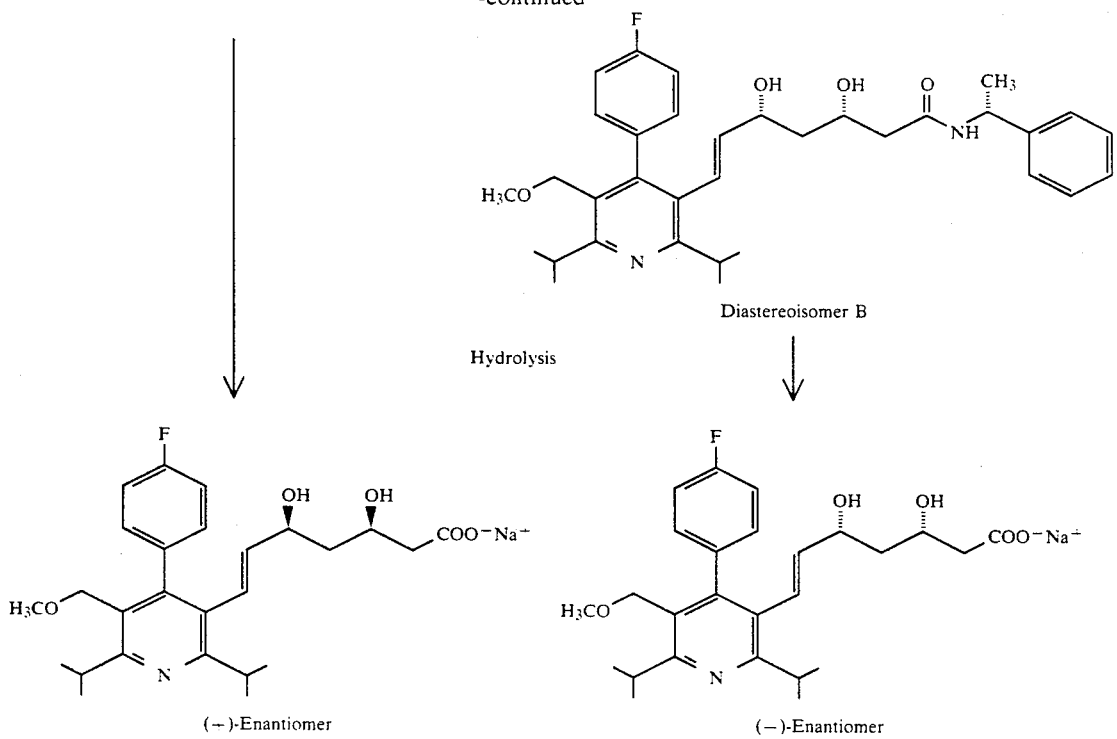

Diastereoisomer B

Hydrolysis (−)-Enantiomer (−)-Enantiomer

The hydrolysis of the esters (II) is in general carried out by treating the esters with bases in inert solvents, the salts in general being formed initially and then being converted into the free acid (I) in a second step by treating with acid.

Suitable solvents for the hydrolysis of the esters are water or the organic solvents customary for hydrolysis of esters. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to employ mixtures of the solvents mentioned.

Suitable bases for the hydrolysis of the esters are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate, or alkali metal alkoxides such as sodium ethoxide, sodium methoxide, potassium methoxide, potassium ethoxide or potassium tert.-butoxide. Sodium hydroxide or potassium hydroxide are particularly preferably employed.

Hydrolysis of the esters is in general carried out in a temperature range from −10 ° C. to 100° C., preferably from +20° C. to +80° C.

Hydrolysis of the esters is in general carried out at normal pressure. However, it is also possible to work at reduced pressure or at elevated pressure (for example from 0.5 to 5 bar).

When carrying out the hydrolysis, the base is in general employed in an amount of 1 to 3 mol, preferably of 1 to 5 mol, relative to 1 mol of the ester. Molar amounts of reactants are particularly preferably used.

When carrying out the hydrolysis, the salts of the acid according to the invention are formed in the first step and can be isolated. The acid according to the invention is obtained by treating the salts with customary inorganic acids. These preferably include mineral acids such as, for example, hydrochloric acid, hydrobromic acid, sulphuric acid or phosphoric acid. It has proven advantageous in this case in the preparation of the carboxylic acid to acidify the basic reaction mixture from the hydrolysis in a second step without isolation of the salts. The acid can then be isolated in a customary manner.

The reaction of the esters (II) with the enantiomerically pure amines (III) to give the diastereomeric amides (IV) is in general carried out in inert solvents.

Suitable solvents for this purpose ar the organic solvents customary for amidations. These preferably include ethers such as diethyl ether, dioxane or tetrahydrofuran, or chlorinated hydrocarbons such as methylene chloride or chloroform, or dimethylformamide. However, the corresponding amine (III) is particularly preferably employed in excess, if desired with tetrahydrofuran or dioxane as solvent.

The reaction is in general carried out in a temperature range from 0° C. to 100° C., preferably from +20° C. to +80° C.

The reaction is in general carried out at normal pressure, but it is also possible to work at reduced pressure or elevated pressure.

It has proved advantageous in the reaction either to employ the amine directly as the solvent in a very large excess, or else when using a further solvent to work in an excess of up to 10-fold.

The hydrolysis of the diastereomeric amides (IV) is carried out by customary methods, for example by treating the amides with bases or acids in inert solvents.

Suitable inert solvents for this purpose are water and/or organic solvents. Organic solvents which may be preferably mentioned are alcohols such as methanol, ethanol, propanol or isopropanol, or ethers such as diethyl ether, dioxane or tetrahydrofuran. Water and water/alcohol mixtures are particularly preferred.

Suitable acids for the hydrolysis of the amides are the customary inorganic or organic acids. Hydrochloric acid, hydrobromic acid, sulphuric acid and methanesulphonic acid or toluenesulphonic acid are preferably used here.

Suitable bases for the hydrolysis of the amides are the customary inorganic bases such as sodium hydroxide or potassium hydroxide or sodium methoxide or ethoxide or potassium methoxide or ethoxide or sodium carbonate or potassium carbonate.

In the case of the phenethylamides, the hydrolysis of the amides is preferably carried out in ethanolic hydrochloric acid and in the case of the phenylglycinolamides with sodium hydroxide solution, if desired in the presence of alcohol.

Hydrolysis of the diastereomeric amides (IV) is in general carried out in a temperature range from 0° C. to 150° C., preferably from +20° C. to +100° C.

Hydrolysis of the amides is in general carried out at normal pressure, but can also be carried out at elevated or reduced pressure.

It is moreover also possible to prepare the enantiomerically pure salts of the formula (I) by separating the corresponding racemates by customary methods of chromatography.

The amines (III) employed as starting substances are known or can be prepared by methods known per se. Preferably, amines of the formula (III) according to the invention are employed in which $R^3$ represents hydrogen and $R^2$ represents methyl or hydroxymethyl.

The diastereomeric amides (IV) are new. They are useful intermediates for the preparation of the enantiomerically pure substituted pyridyl-dihydroxy-heptenoic acid and its salts.

The substituted pyridyl-dihydroxy-heptenoic acid according to the invention, its salts and isomeric forms have useful pharmacological properties which are superior compared with the prior art, in particular they are highly active inhibitors of 3-hydroxy-3-methyl-glutaryl coenzyme A (HMG-CoA) reductase and as a result thereof inhibitors of cholesterol biosynthesis. They can therefore be employed for the treatment of hyperlipoproteinaemia or arteriosclerosis. The active compounds according to the invention additionally bring about a lowering of the cholesterol content in the blood.

The pharmacological action of the substances according to the invention was determined in the following tests:

A) The enzyme activity determination was carried out, in modified form, according to G. C. Ness et al., Archives of Biochemistry and Biophysics 197, 493-499 (1979). Male Rico rats (body weight 300 to 400 g) were treated for 11 days with altromin powdered feed, to which 40 g of cholestyramine/kg of feed had been added. After decapitation, the liver was removed from the animals, and placed on ice. The livers were comminuted and homogenized 3 times in a Potter-Elvejem homogenizer in 3 volumes of 0.1 M sucrose, 0.05 M KCl, 0.04 M $K_xH_y$phosphate (mixture of $K_2HPO_4$ and $KH_2PO_4$ of pH 7.2), 0.03 M ethylenediaminetetraacetic acid, 0.002 M dithiothreitol (SPE) buffer (sucrose-phosphate-ethylenediaminetetraacetic acid buffer) pH 7.2. The homogenizate was then centrifuged for 15 minutes and the sediment was discarded. The supernatant was sedimented at 100,000 g for 75 minutes. The pellet is taken up in ¼ volume of SPE buffer, homogenized again and then centrifuged again for 60 minutes. The pellet is taken up with a 5-fold amount of its volume of SPE buffer, homogenized and frozen and stored at −78° C. (enzyme solution).

For testing, the test compounds (or mevinolin as reference substance) were dissolved in dimethylformamide with the addition of 5 vol-% of 1 N NaOH and employed in various concentrations in the enzyme test using 10 µl. The test was started after preincubation of the compounds with the enzyme at 37° C. for 20 minutes. The test batch was 0.380 ml and contained 4 µmol of glucose-6-phosphate, 1.1 mg of bovine serum albumin, 2.1 µmol of dithiothreitol, 0.35 µmol of NADP (β-nicotinamide adenine dinucleotide phosphate), 1 unit of glucose-6-phosphate dehydrogenase, 35 µmol of $K_xH_y$ phosphate pH 7.2, 20 µl of enzyme preparation and 56 nmol of 3-hydroxy-3-methylglutaryl coenzyme A (glutaryl-3-$^{14}$C) 100,000 dpm. The mixture was incubated at 37° C. for 60 minutes and the reaction was stopped by addition of 300 µl of 0.25 M HCl. After a post-incubation of 60 minutes at 37° C., the batch was centrifuged and 600 µl of the supernatant was applied to a 0.7×4 cm column packed with 5-chloride anion exchanger having a particle size of 100 to 200 mesh. The column was washed with 2 ml of dist. water and runnings plus washing water were treated with 3 ml of a scintillation fluid and counted in a scintillation counter. $IC_{50}$ values were determined by intrapolation by plotting the percentage inhibition against the concentration of the compound in the test. To determine the relative inhibitory potency, the $IC_{50}$ value of the reference substance mevinolin was set at 100 and compared with the simultaneously determined $IC_{50}$ value of the test compound.

B) The subchronic action of the compounds according to the invention on the blood cholesterol values of dogs was tested in feeding experiments of several weeks duration. For this, the substance to be investigated was given p.o. once daily in a capsule to healthy beagle dogs together with the feed over a period of time lasting several weeks. colestyramine (4 g/100 g of feed) as the gallic acid sequestrant was additionally admixed in the feed during the entire experimental period, i.e., before during and after the administration period of the substances to be investigated. Venous blood was taken from the dogs twice weekly and the serum cholesterol was determined enzymatically using a commercial test kit. The serum cholesterol values during the administration period were compared with the serum cholesterol values before the administration period (controls).

The present invention also includes pharmaceutical preparations which contain one or more compounds of the general formula (I) in addition to inert, non-toxic, pharmaceutically suitable auxiliaries and excipients or which consist of one or more active compounds of the formula (I), and processes for the production of these preparations.

The active compounds of the formula (I) should be present in these preparations in a concentration of 0.1 to 99.5% by weight, preferably from 0.5 to 95% by weight of the total mixture.

In addition to the active compounds of the formula (I), the pharmaceutical preparations can also contain other pharmaceutical active compounds.

The abovementioned pharmaceutical preparations can be prepared in a customary manner by known methods, for example using the auxiliary(ies) or excipient(s).

In general, it has proved advantageous to administer the active compound(s) of the formula (I) in total amounts from about 0.1 μg/kg to about 100 μg/kg, preferably in total amounts from about 1 μg/kg to 50 μg/kg of body weight every 24 hours, if appropriate in the form of several individual doses, to achieve the desired result.

However, it may be advantageous to deviate from the amounts mentioned, in particular depending on the species and the body weight of the subject treated, on individual behavior towards the medicament, the nature and severity of the disease, the type of preparation and administration, and the time or interval at which administration takes place.

EXEMPLARY EMBODIMENTS

Example 1

Sodium 3R,5S-(+)-erythro-(E)-7-[4-(4-fluorophenyl)-2,6-diisopropyl-5-methoxymethyl-pyrid-3-yl]-3,5-dihydroxyhept-6-enoate

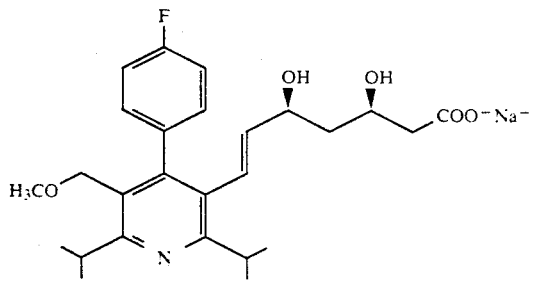

and

Example 2

Sodium 3S,5R-(−)-erythro-(E)-7-[4-(*4-fluorophenyl)-2,6-diisopropyl-5-methoxymethyl-pyrid-3-yl]-3,5-dihydroxyhept-6-enoate

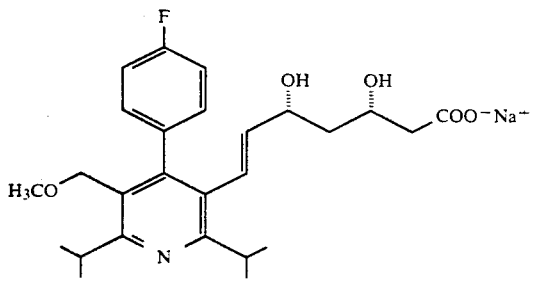

Process variant A - Racemate separation using R-(+)-phenylethylamine a) Preparation and separation of the diastereomeric phenethylamides

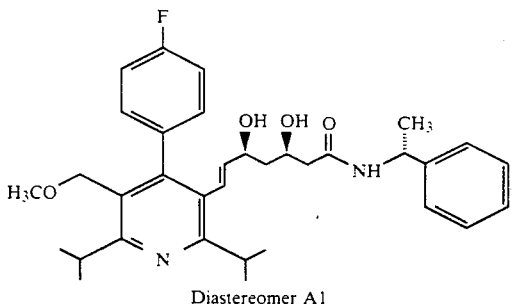

Diastereomer A1

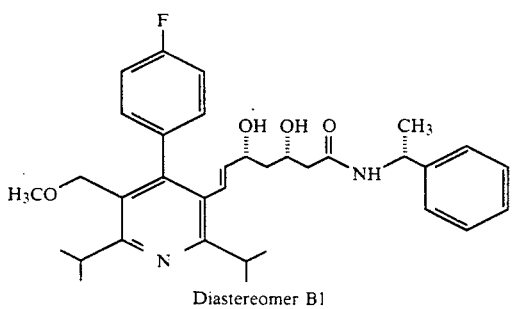

Diastereomer B1

4.7 g (10 mmol) of methyl erythro-(E)-4-(4-fluorophenyl)-2,6-diisopropyl-5-methoxymethylpyrid-3-yl]-3,5-dihydroxy-hept-6-enoate are dissolved in 20 ml of R-(+)-phenethylamine and heated at 40° C. for 72 h. The reaction solution is poured into 150 ml of water and the solution is adjusted to pH 4 with 1 N hydrochloric acid. It is then extracted several times with ether. The combined organic extracts are washed with saturated sodium chloride solution, dried over magnesium sulphate and concentrated. After prepurification on silica gel 63-200 μ (eluent ethyl acetate/petroleum ether 4:6→6:4), the residue is separated on a 15 μ pre-packed column (eluent ethyl acetate/petroleum ether 1:1).

Yield: 2.1 g of diastereomer A1 (37.4% of theory), 1.5 g of diastereomer B1 (26.6% of theory).

b) Preparation of the enantiomerically pure sodium salts (Ex. ½)

2.1 g (3.7 mmol) of the diastereomer A1 are dissolved in 70 ml of 15% strength ethanol and, after addition of 13 ml of 1 N hydrochloric acid, heated under reflux for 48 h. After cooling, the supernatant solution is filtered off and the residue is stirred several times with ethanol. The combined ethanol solutions are concentrated and the residue is taken up in 50 ml of water and 50 ml of dichloromethane. The pH of the solution is adjusted to 3.5 using 1 N hydrochloric acid and the solution is then extracted several times with dichloromethane. The combined organic solutions are dried over sodium sulphate and concentrated. The residue is taken up in 50 ml of tetrahydrofuran/water 1:1 and the pH of the solution is adjusted to 7.5 using 1 N sodium hydroxide solution. The tetrahydrofuran is evaporated on a rotary evaporator and the remaining aqueous solution is lyophilised. The crude lyophilisate is purified on RP 18 (eluent: acetonitrile/water 30:70). After freeze-drying of the product fractions, 850 mg (48% of theory) of the (+)-enantiomeric sodium salt (Ex. 1) are obtained.

$^1$H-NMR (DMSO-d$_6$): δ (ppm)=1.0 (m, 1H); 1.23 (d, 6H); 1.28 (d, 6H); 1.3 (m, 1H); 15 (dd, 1H); 1.98 (dd, 1H); 3.07 (s, 3H); 3.2-3.4 (m, 3H); 3.52 (m, 1H); 4.02 (m, 2H); 5.28 (dd, 1H; 6.17 (d, 1H); 7.1-7.3 (m, 4H).

Specific rotation (EtOH): $[\alpha]^{20}_D = 24.1°$ (c=1.0).

800 mg (61.5% of theory) of the (−)-enantiomeric sodium salt (Ex. 2) are obtained as described above from 1.5 g (2.6 mmol) of the diastereomer B1.

Specific rotation (EtOH): $[\alpha]^{20}_D = -23.2°$ (c=1.0).

Process variant B - Racemate separation using S-(+)-phenylglycinol a) Preparation of the diastereomeric phenylglycinolamides

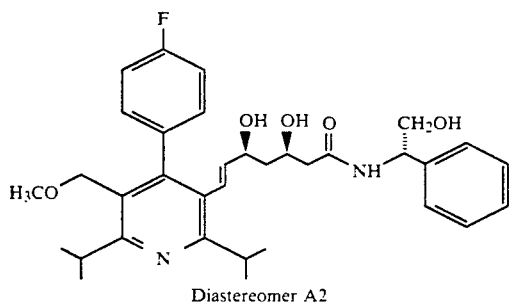

Diastereomer A2

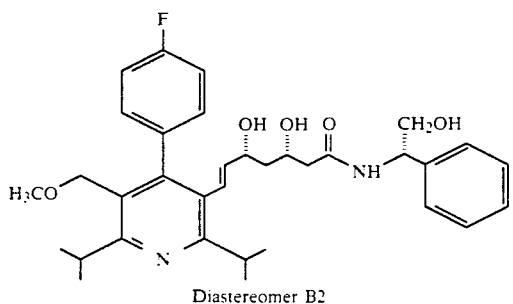

Diastereomer B2

418 g (0.88 mol) of methyl erythro-(E)-7-[4-(4-fluorophenyl)-2,6-diisopropyl-5-methoxymethyl-pyrid-3-yl]-3,5-dihydroxy-hept-6-enoate and 360 g (2.6 mol) of S-(+)-phenylglycinol are dissolved in 1 l of absol. tetrahydrofuran and the mixture is heated to 50° C. for 96 h. After cooling to room temperature, 1 l of water is added, and the solution is adjusted to pH 4 using 5 N hydrochloric acid and extracted 3 times using 400 ml of ether each time. The combined organic phases are washed with 400 ml of saturated sodium chloride solution, dried over sodium sulphate and concentrated on a rotary evaporator. The residue (500 g of crude product) is preseparated (eluent ethyl acetate/petroleum ether 8:2) into two portions on a column (in each case about 1.8 kg of silica gel). 350 g of prepurified crude product are thus obtained, which consists almost exclusively of the two diastereoisomeric amides. The prepurified crude product is separated into 7×50 g portions on a silica gel column (Büchi column, length 63 cm, 7 cm, silica gel 20 sample application via a 100 ml sample loop). Yield: 195 g (38.2% of theory) of the diastereomer A2. The diastereomer B2 was not isolated pure, but was recovered as a crude product for possible later use on washing the columns.

b) Preparation of the enantiomerically pure sodium salts (Ex. ½)

195 g (0.34 mol) of the diastereomerically pure amide A2 are dissolved in 1 l of ethanol p.A. and, after addition of 1.2 l of 1 N sodium hydroxide solution, the mixture is heated overnight under reflux. After cooling to room temperature, the supernatant solution is decanted off and the oily residue is stirred 3 times using 50 ml of ethanol p.A. each time. The solutions are combined and concentrated. The residue is taken up in 500 ml of water and 500 ml of methylene chloride and the solution is adjusted to pH 3.5 using 1 N hydrochloric acid. The organic phase is then separated off and the aqueous phase is extracted 3 times using 400 ml of methylene chloride each time. The combined organic phases are dried ($Na_2SO_4$) and concentrated. The residue is dissolved in 100 ml of tetrahydrofuran and the solution is diluted with 500 ml of water. It is then adjusted to pH 7.5 using 1 N sodium hydroxide solution, the tetrahydrofuran is removed on a rotary evaporator and the aqueous solution which remains is lyophilised.

142 g of crude lyophilisate are obtained which, for desalting, are further purified and desalted in 27×5 g portions and 2×3.5 g portions on an RP 18 column (length 40 cm, ⌀3 cm, silica gel RP 18, 30 μ, eluent acetonitrile/water 30:70). All product fractions are combined, the acetonitrile is removed on a rotary evaporator and the aqueous residue is lyophilised.

Yield: 102 g (62.5% of theory) of the (+)-enantiomeric sodium salt (Ex. 1).

We claim:

1. Substituted pyridyl-dihydroxy-heptenoic acid of the formula

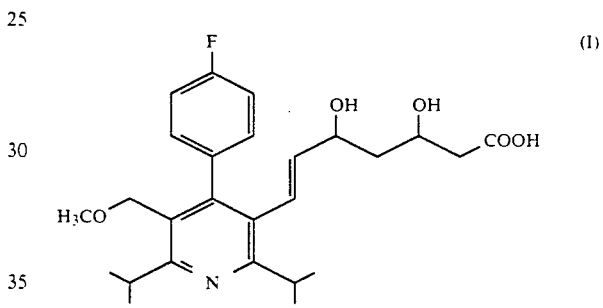

or a pharmaceutically acceptable salt thereof.

2. Substituted pyridyl-dihydroxy-heptenoic acid of the formula (I) according to claim 1 and its salts in the erythro configuration.

3. (+)-Enantiomers of the substituted pyridyldihydroxy-heptenoic acid of the formula (I) according to claim 1 and its salts.

4. (+)-Enantiomers of substituted pyridyl-dihydroxyheptenoic acid of the formula (I) according to claim 1 and its salts in the erythro configuration.

5. Sodium, potassium, magnesium and ammonium salts of the substituted pyridyl-dihydroxy-heptenoic acid of the formula (I) according to claim 1.

6. Sodium 3R,5S-(+)-erythro-(E)-7-[4-(4-fluorophenyl)-2,6-diisopropyl-5-methoxymethyl-pyrid -3-yl]-3,5-dihydroxy-hept-6-enoate.

7. Diastereomeric amides of the formula

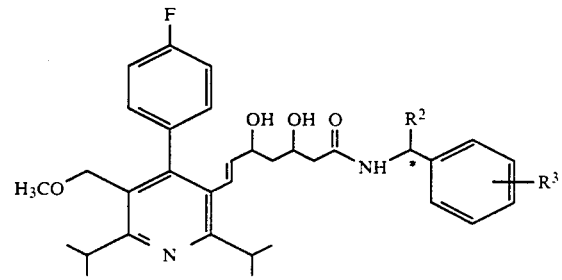

in which $R^2$ represents $C_1$–$C_4$-alkyl which is optionally substituted by hydroxyl, and $R^3$ represents hydrogen, $C_1$–$C_4$-alkyl, halogen or $C_1$–$C_4$-alkoxy.

8. A composition for inhibiting 3-hydroxy-3-methyl-glutaryl coenzyme A which comprises a compound or salt thereof according to claim 1 and a pharmaceutically acceptable diluent.

9. A method of inhibiting 3-hydroxy-3-methyl-glutaryl coenzyme A in a patient in need thereof which comprises administering to said patient an amount effective therefore of a compound or salt thereof according to claim 1.

* * * * *